United States Patent
Young

(10) Patent No.: US 9,428,318 B2
(45) Date of Patent: Aug. 30, 2016

(54) POUCH FOR INTERNAL MIXTURE OF SEGREGATED REACTANTS AND APPLICATIONS THEREOF

(75) Inventor: Daniel Young, Henderson, NV (US)

(73) Assignee: FOREVER YOUNG INTERNATIONAL, INC., Henderson, NV (US)

(*) Notice: Subject to any disclaimer, the term of this patent is extended or adjusted under 35 U.S.C. 154(b) by 1254 days.

(21) Appl. No.: 13/261,146

(22) PCT Filed: Mar. 19, 2010

(86) PCT No.: PCT/US2010/028033
§ 371 (c)(1),
(2), (4) Date: Apr. 10, 2012

(87) PCT Pub. No.: WO2010/108132
PCT Pub. Date: Sep. 23, 2010

(65) Prior Publication Data
US 2012/0180777 A1     Jul. 19, 2012

Related U.S. Application Data

(60) Provisional application No. 61/161,745, filed on Mar. 19, 2009.

(51) Int. Cl.
*B65D 81/32* (2006.01)
*B65D 75/30* (2006.01)
(Continued)

(52) U.S. Cl.
CPC ............ *B65D 81/3266* (2013.01); *A47J 36/28* (2013.01); *B65D 75/30* (2013.01); *B65D 81/3272* (2013.01); *B65D 81/3484* (2013.01); *F24J 1/00* (2013.01); *C09K 5/18* (2013.01)

(58) Field of Classification Search
CPC ....... F24J 1/00; A47J 36/28; B65D 81/3484; B65D 81/3266; B65D 75/30; F25D 5/00; F25D 5/02; C09K 5/18

USPC ............ 126/263.01, 263.05, 263.06, 263.07, 126/263.08, 263.09
See application file for complete search history.

(56) References Cited

U.S. PATENT DOCUMENTS 2,157,169 A * 5/1939 Foster ...................... 126/263.01
3,085,681 A * 4/1963 Fazzari ......................... 206/222
(Continued)

FOREIGN PATENT DOCUMENTS

JP     2008035919 A     2/2008
JP     2008133353 A     6/2008

OTHER PUBLICATIONS

International Bureau, International Search Report for International Application No. PCT/US2010/028033, Sep. 23, 2010, pp. 1-3, Geneva, Switzerland.
(Continued)

*Primary Examiner* — David J Laux
(74) *Attorney, Agent, or Firm* — Troutman Sanders, LLP

(57) ABSTRACT

A pouch for internal mixture of segregated reactants includes an outer containment envelope with a sealed reactant compartment inside. A middle shear strip and two outer strips, together defining two shear lines, are connected to the reactant compartment. The outer strips are folded under the reactant compartment with their tips anchored to the containment envelope. The middle strip extends away from the reactant compartment and through a slit in the containment envelope. Pulling on the middle strip causes the shear lines to lengthen until the reactant compartment is shorn open to release a reactant. A permeable second reactant compartment containing a second reactant may also be disposed inside the containment envelope, and may include a slit through which the middle strip passes. The reaction in the pouch may be exothermic and the pouch may be applied to any object to be heated such as a wet wipes dispenser.

11 Claims, 11 Drawing Sheets

(51) Int. Cl.
*A47J 36/28* (2006.01)
*B65D 81/34* (2006.01)
*F24J 1/00* (2006.01)
*C09K 5/18* (2006.01)

(56) References Cited

U.S. PATENT DOCUMENTS

| | | | | |
|---|---|---|---|---|
| 3,149,943 | A * | 9/1964 | Amador | A61F 7/106 |
| | | | | 126/263.09 |
| 3,272,324 | A * | 9/1966 | Schneider et al. | 206/221 |
| 3,674,134 | A * | 7/1972 | Turner | 206/219 |
| 3,763,622 | A * | 10/1973 | Stanley, Jr. | 53/431 |
| 3,836,039 | A | 9/1974 | Seiferth et al. | |
| 4,106,478 | A * | 8/1978 | Higashijima | 149/15 |
| 4,559,921 | A * | 12/1985 | Benmussa | 126/263.09 |
| 4,856,651 | A * | 8/1989 | Francis, Jr. | 206/219 |
| 5,693,638 | A | 12/1997 | Myers | |
| 8,118,021 | B2 | 2/2012 | Cho et al. | |
| 2002/0012762 | A1 | 1/2002 | Bunyan | |
| 2003/0000517 | A1 | 1/2003 | Joseph et al. | |
| 2003/0116452 | A1 | 6/2003 | Saric et al. | |
| 2005/0224388 | A1 * | 10/2005 | Saric et al. | 206/554 |
| 2006/0005827 | A1 * | 1/2006 | Consoli et al. | 126/263.06 |
| 2008/0128431 | A1 * | 6/2008 | Gradzewicz | 220/592.01 |

OTHER PUBLICATIONS

International Bureau, International Preliminary Report on Patentability Chapter I for International Application No. PCT/US2010/028033, Sep. 19, 2011, pp. 1-12, Geneva, Switzerland.

International Bureau, Written Opinion of the International Search Authority for International Application No. PCT/US2010/028033, Sep. 19, 2011, pp. 1-11, Geneva, Switzerland.

* cited by examiner

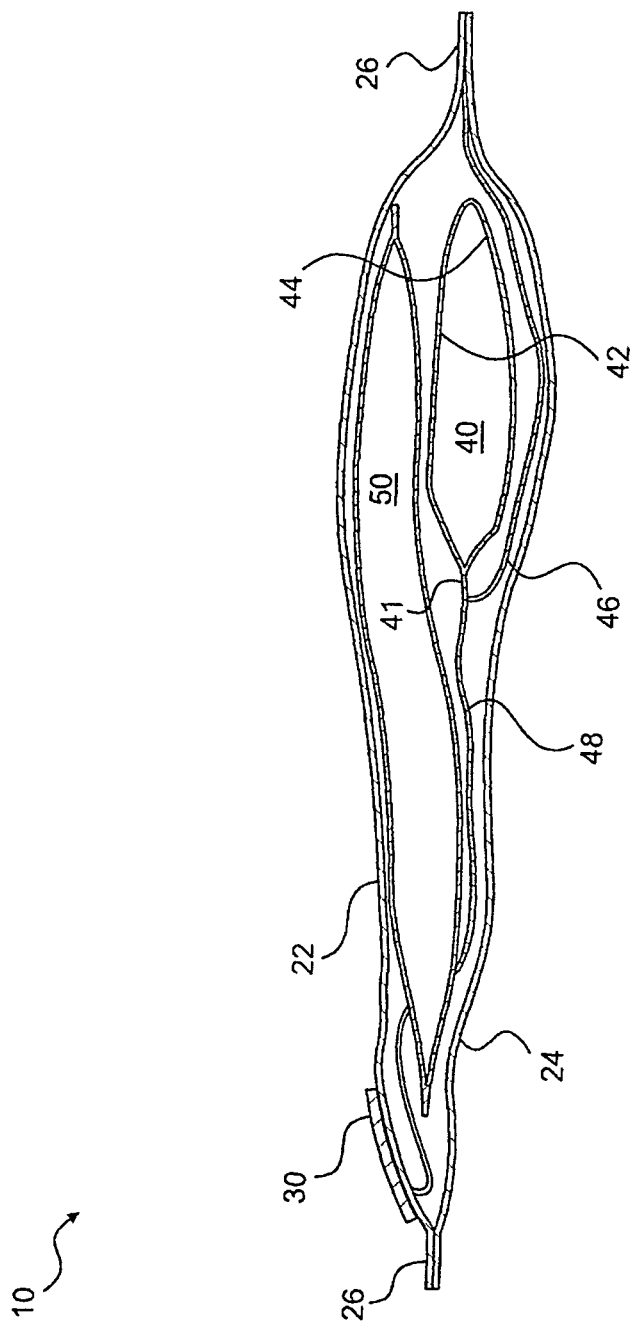

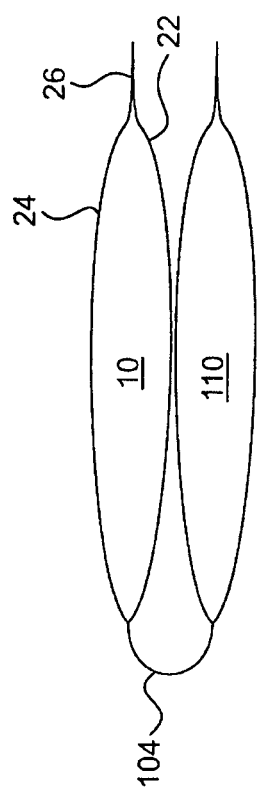

POUCH FOR INTERNAL MIXTURE OF SEGREGATED REACTANTS AND APPLICATIONS THEREOF

CROSS-REFERENCE TO RELATED APPLICATIONS

This application is a United States national stage entry of International Application PCT/US10/28033 entitled "Pouch for Internal Mixture of Segregated Reactants and Applications Thereof" and filed on Mar. 19, 2010, which claims priority to U.S. provisional patent application 61/161,745 entitled "Pouch for Internal Mixture of Segregated Reactants and Applications Thereof" and filed on Mar. 19, 2009. The contents of these prior applications are incorporated into this application in their entirety.

FIELD

The following description relates generally to pouches for internal mixture of segregated reactants, and more particularly to pouches with shearable internal compartments.

BACKGROUND

Devices incorporating internal chemical reactants contained in pouches, particularly for the generation of exothermic or endothermic reactions, have been commercially available for some time. These devices all contain at least two reactants which need to be kept separate until the desired time of activation, at which point the barrier(s) separating the reactants must be broken to allow the reactants to mix.

One typical manufacturing design of these types of pouches incorporates a frangible seal separating the reactants inside the pouch. A frangible seal is a seal that tends to fracture, break, crumble and/or fall apart, as opposed to stretching, twisting and/or plastically deforming, when the seal is placed under stress. In such a pouch, the frangible seal that keeps the reactants separate consists of a partially heat-sealed line between two sealable layers of film forming separate side-by-side chambers or reservoirs for the reactants, with the dividing seal line being a weaker bond between the sealable layers than the surrounding film or the perimeter seals which form the outer closures or sealed edges. With external force applied in a compressive action on the pouch, the design is such that the partially sealed line between the chambers would fail, allowing the liquid or liquids to migrate between the chambers, thus mixing and reacting to generate the required results. In other words, the user would place the pouch on a flat surface and press firmly with the flat of their hands to build enough internal pressure to rupture the internal seal.

There are inherent problems with this design. For example, the amount of force needed to rupture the dividing seal can sometimes not be met by a smaller, weaker or inexperienced user. A certain technique is required and an understanding of where to push and the required forces helps the user to press material against the center dividing seal so that the force is directed against the area where it is designed to fail. Additionally, even though the dividing seal is ruptured, sometimes only a partial mixing of the reactants occurs. Typically, the internal materials are not visible to the user, and therefore when the user feels the pressure release due to a failure of the inner dividing seal, they fail to massage the contents thoroughly to provide complete mixing, leaving much of the original materials in their respective chambers.

Furthermore, the dividing seal, which has to be strong enough to keep the materials separated during storage and transportation, but weak enough for the user to cause to fail with compression force, refuses to burst with any sort of pressure short of a critical failure of the surrounding film. In other words, the perimeter seals or the film itself may burst before the inner seal releases, thereby creating leaks, a mess and a failed activation.

Finally, quite often in an attempt to make it easier for the user to activate, the manufacturer will create a weaker seal which will fail with less pressure from the user. Many times, these seals will fail prematurely due to outside forces encountered during shipping and storage or at lowered atmospheric pressures such as during air cargo transportation, causing a defective product, and in certain situations, a dangerous result, depending on the contents. During manufacturing, it is also difficult to control the partial seal parameters required and hold that consistency throughout a production run. The manufacturing process needs to be very tightly controlled to achieve a reliable result. Yet even when the product is manufactured to correct specifications, the final result is very much operator dependant.

Another method of construction known in the art is a simple pouch within a pouch design where one reactant is loose in the outer pouch and the other, typically a liquid, is contained in the inner pouch, which is also disposed within the outer pouch. Much the same as the previous example, the user must cause the inner pouch to burst and release its contents without damaging the outer pouch. Sometimes the user must press the article flat on a surface as the previous example, or an alternative method is to twist the entire package to put stress on the inner pouch to overcome its integrity and cause it to leak into the outer pouch. One again, it is difficult to predict the point of failure and the aperture size and shape. Since again, this process is invisible to the user, failure to rupture or inadequate mixing is a likely outcome. And once again, people with weaker or smaller hands or lack of experience may have trouble rupturing the inner pouch.

Yet another problem with known pouches for internal mixing of reactants is their lack of ability to vent any byproduct gasses created by the chemical reaction. If any such gasses are not permitted to escape from the reaction chamber to the outside environment, a ballooning effect and dangerous catastrophic failure of the outer package may occur. For this reason the types of reactants that may be used in these pouches is severely limited because manufacturers cannot use chemicals that release significant amounts of gas during reaction.

There is a need for an improved design and construction of a pouch for internal mixture of segregated reactants that comprises one or more secure and separate reactant storage compartments that are safely and easily unsealed by a user who lacks size, strength, experience, and technical knowledge. Furthermore, there is a need for a pouch for internal mixture of segregated reactants that incorporates a venting system to open the spectrum of available reactants to include those that cause significant out-gassing.

SUMMARY

The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, a pouch for internal mixture of segregated reactants includes an outer containment envelope with a sealed reactant compartment inside. A middle shear strip and two outer strips, together defining two shear lines, are connected to the reactant compartment. The outer strips are folded under the reactant compartment with their tips anchored to the containment envelope. The middle strip extends away from the reactant compartment and through a slit in the containment envelope. Pulling on the middle strip causes the shear lines to lengthen until the reactant compartment is shorn open to release a reactant. A permeable second reactant compartment containing a second reactant may also be disposed inside the containment envelope, and may include a slit through which the middle strip passes. The reaction in the pouch may be exothermic and the pouch may be applied to any object to be heated such as a wet wipes dispenser.

The pouch may also include a second reactant compartment disposed inside the outer containment envelope adjacent the first sealed reactant compartment and containing a second reactant. The second reactant compartment further may include a permeable membrane and a slit passing completely through the second reactant compartment. The middle shear strip may pass through the slit in the second reactant compartment. The first reactant may be a liquid that is released onto the permeable membrane of the second reactant compartment when the middle shear strip is pulled, thereby mixing the first reactant with the second reactant. The second reactant compartment may form a barrier that prevents the first reactant from escaping through the slit in the outer containment envelope, but which may permit gasses to escape, after the tip of the middle shear strip is pulled.

Mixing the first reactant with the second reactant may create an exothermic (or endothermic) reaction that causes the pouch to emit (absorb) heat. The outer containment envelope of the heat emitting pouch may be connected to a product dispenser in order to heat the products inside. For example, the product dispenser may be a wet wipe dispenser having a substantially flat dispensing surface with a dispensing aperture through which wet wipes are dispensed. The outer containment envelope of the pouch may be hinged to the wet wipe dispenser to permit the outer containment envelope to rotate onto and lie flat on the dispensing surface and to rotate off the dispensing surface to uncover the dispensing aperture. The outer containment envelope may include a substantially flat adhesive surface that may be adhered to an object to be heated. The outer containment envelope may be adhered to an object to be heated with a thermal transfer silicone-based adhesive.

The middle shear strip connected to the sealed reactant compartment may include an adhesive tab attached to the tip of the middle shear strip and adhered to an outer surface of the first layer of the outer containment envelope and around the slit in the first layer of the outer containment envelope to hermetically seal the slit of the outer containment envelope. The tips of the two outer strips may be anchored inside the outer containment envelope to the periphery of the outer containment envelope. The sealed reactant compartment may include a first transverse seal that is broken by at least one of the at least two shear lines when the tip of the middle shear strip is pulled. Further, the sealed reactant compartment may include first and second separate chambers separated by a second transverse seal that is broken by at least one of the at least two shear lines when the tip of the middle strip is pulled. The first chamber of the sealed reactant compartment may contain the first reactant while the second chamber may contain a second reactant.

In another aspect of the disclosed embodiments, a self-heating wet wipe dispenser includes a wet wipe dispenser having a substantially flat dispensing surface with a dispensing aperture through which wet wipes are dispensed. A heating unit is placed in contact with the wet wipe dispenser. The heating unit has an outer containment envelope with a first layer bonded to a second layer around the periphery of the outer containment envelope. The outer containment envelope contains a first reactant and a sealed reactant compartment which contains a second reactant. The sealed reactant compartment has a predetermined seal failure region. When a user causes the predetermined seal failure region of the sealed reactant compartment to fail, the second reactant escapes from the sealed reactant compartment and mixes with the first reactant in the outer containment envelope to create an exothermic reaction that heats the wet wipe dispenser.

The first layer of the outer containment envelope of the self-heating wet wipe dispenser may include a slit. At least three strips may be connected to the sealed reactant compartment, including a middle shear strip separated from two outer strips by two shear lines. The two outer strips may be folded under the sealed reactant compartment with their tips anchored to the outer containment envelope. The tips of the two outer strips may be anchored inside the outer containment envelope to the periphery of the outer containment envelope. The middle shear strip may extend away from the sealed reactant compartment and through the slit in the first layer of the outer containment envelope so that the tip of the middle shear strip is outside the outer containment envelope. The user may cause the predetermined seal failure region of the sealed reactant compartment to fail by pulling on the tip of the middle shear strip causing the two shear lines to lengthen until shearing the predetermined failure region of the sealed reactant compartment. The first reactant may be contained in a permeable compartment inside the outer containment envelope.

In yet another aspect of the disclosed embodiments, a pouch for internal mixture of segregated reactants includes an outer containment envelope with a first layer bonded to a second layer around the periphery of the outer containment envelope. The first layer of the outer containment envelope has a slit. A sealed reactant compartment is disposed inside the outer containment envelope and contains a first reactant. At least two strips are connected to the sealed reactant compartment and include a shear strip separated from an outer strip by a shear line, the shear strip and the outer strip each having a tip. The outer strip is folded under the sealed reactant compartment with its tip anchored to the outer containment envelope. The shear strip extends away from the sealed reactant compartment and through the slit in the first layer of the outer containment envelope so that the tip of the shear strip is disposed outside the outer containment envelope. Pulling on the tip of the shear strip causes the shear line to lengthen until the sealed reactant compartment is shorn open and releases the first reactant into the outer containment envelope.

The pouch may further include a second reactant compartment disposed inside the outer containment envelope adjacent the first sealed reactant compartment and containing a second reactant. The second reactant compartment includes a permeable membrane and a slit passing completely through the second reactant compartment. The shear strip passes through the slit in the second reactant compartment. The first reactant may be a liquid that is released onto the permeable membrane of the second reactant compartment when the shear strip is pulled, thereby mixing the first reactant with the second reactant. The second reactant compartment may form a barrier that prevents the first reactant from escaping through the slit in the outer containment envelope after the tip of the shear strip is pulled. The slit in the outer containment envelope may permit reaction gasses to escape. Mixing the first reactant with the second reactant may create an exothermic reaction so that the pouch emits heat.

The outer containment envelope of the pouch may be connected to an object to be heated. The object to be heated may be a wet wipe dispenser having a substantially flat dispensing surface with a dispensing aperture through which wet wipes are dispensed. The outer containment envelope may be hinged to the wet wipe dispenser to permit the outer containment envelope to lie flat on the dispensing surface and to rotate off the dispensing surface to uncover the dispensing aperture. The outer containment envelope may include a substantially flat adhesive surface, wherein the substantially flat adhesive surface of the outer containment envelope is adhered to the object to be heated. The shear strip may include an adhesive tab attached to the tip of the shear strip and adhered to an outer surface of the first layer of the outer containment envelope and around the slit in the first layer of the outer containment envelope to hermetically seal the slit in the first layer of the outer containment envelope. The tip of the outer strip may be anchored inside the outer containment envelope to the periphery of the outer containment envelope.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

FIG. 3 is a cross-sectional view of the embodiment of FIG. 1.

FIG. 6B is a side elevation view of the embodiment of FIG. 6A, showing the self-heating pouch hinged on top of the dispensing surface of the wet wipe dispenser.

DETAILED DESCRIPTION

A pouch for internal mixture of segregated reactants according to the disclosed embodiments includes an outer containment envelope which contains at least one sealed reactant compartment containing a first reactant. A second reactant is also disposed inside the outer containment envelope, optionally in a permeable compartment. The sealed reactant compartment is connected to a strip which extends outside the outer containment envelope through a slit. When the user pulls on the strip, the sealed reactant compartment is easily shorn open to release the first reactant and allow the first and second reactants to chemically react. The chemical reaction is easily activated by a user without requiring any significant amount of strength or knowledge of the internal structure of the pouch. The slit in the outer containment envelope allows gasses to escape, so a wide variety of reactants may be used in the pouch because there is no danger of the pouch ballooning and/or exploding.

Figure 1:
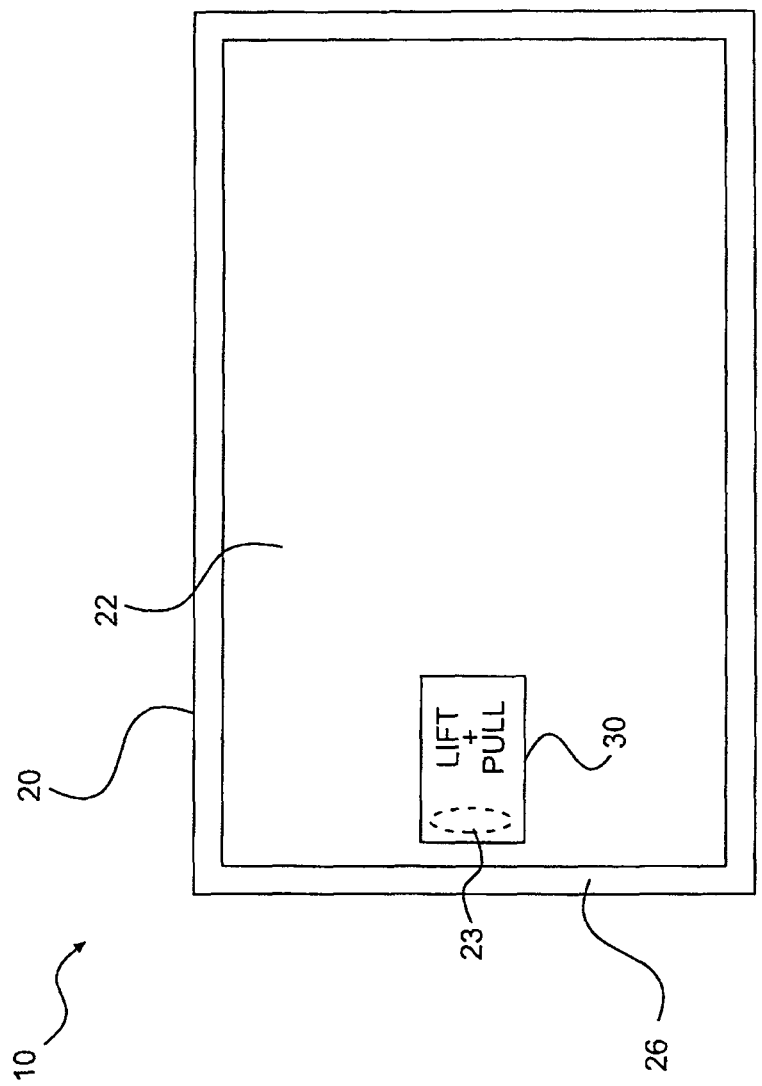
FIG. 1 is a perspective view of one embodiment of a pouch for internal mixture of segregated reactants.

One embodiment of a pouch for internal mixture of segregated reactants is shown in FIG. 1. In this embodiment, pouch 10 includes outer containment envelope 20 which is formed from first layer 22 and second layer 24 (see FIGS. 2 and 3). First layer 22 and second layer 24 are bonded together along the periphery 26 of outer containment envelope 20. The bond between first layer 22 and second layer 24 is air- and watertight so that outer containment envelope 20 is a sealed container. Pull tab 30 is adhered to first layer 22 over slit 23 in first layer 22. Although slit 23 is present in first layer 22, outer containment envelope 20 is nonetheless a sealed container (prior to activation of pouch 10) because pull tab 30 is adhered to the surface of first layer 22 all around slit 23 to hermetically seal outer containment envelope 20.

Figure 2:
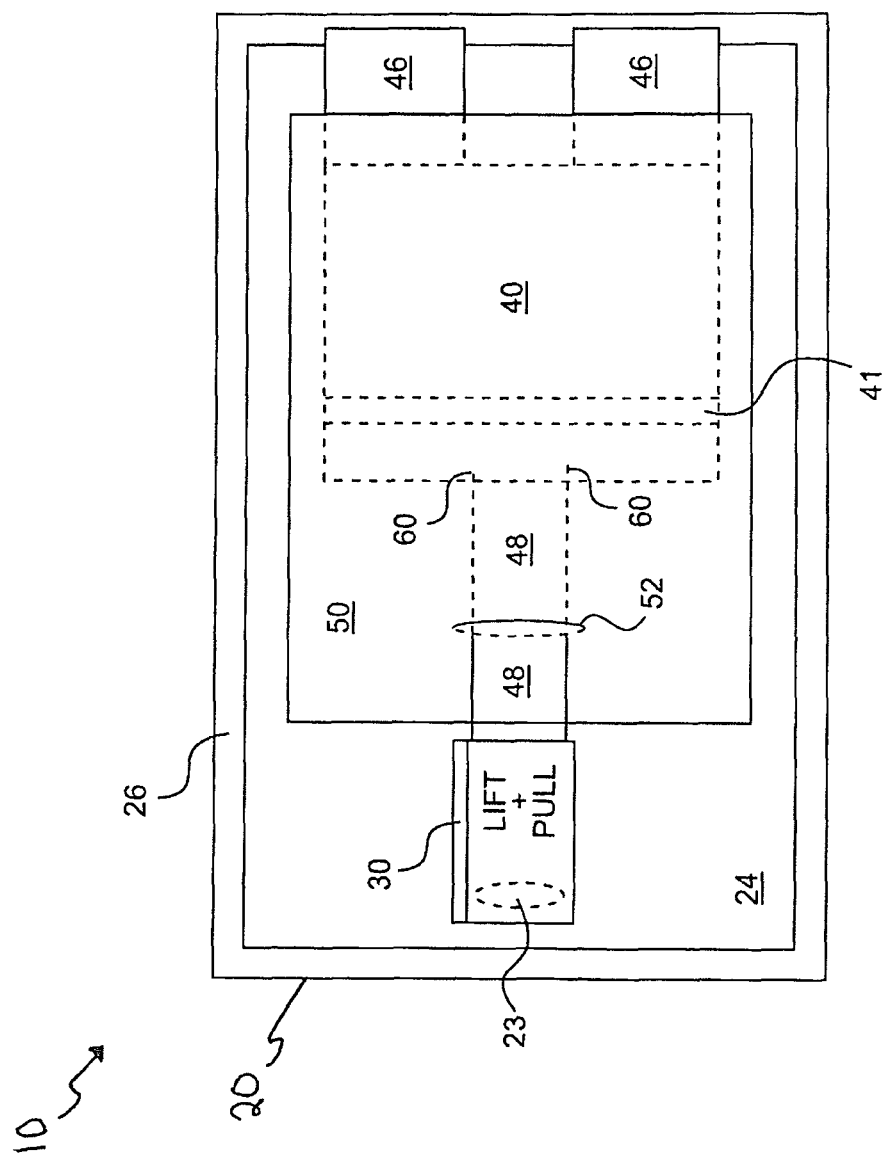
FIG. 2 is a perspective view of the embodiment of FIG. 1, with the top layer of the outer containment envelope not shown in order to reveal the contents of the pouch.

FIG. 2 shows pouch 10 with first layer 22 of outer containment envelope 20 removed in order to reveal the contents of pouch 10. Sealed reactant compartment 40 is shown in hidden lines because it is underneath second reactant compartment 50. Sealed reactant compartment 40 includes transverse seal 41 which segregates the contents of sealed reactant compartment 50 from the inside of outer containment envelope 20. Three strips of material are connected to sealed reactant compartment 40 adjacent to transverse seal 41. Two outer strips 46 are folded under sealed reactant compartment 40 with their tips fixedly anchored inside outer containment envelope 20 to periphery 26 of outer containment envelope 20. The third strip, middle shear strip 48, extends away from sealed reactant compartment 40. The tip of middle shear strip 48 is attached to pull tab 30. Second reactant compartment 50 is disposed on top of sealed reactant compartment 50 and may include a membrane that is permeable to the reactant contained inside sealed reactant compartment 40.

As seen in FIGS. 2 and 3, middle shear strip 48 passes through slit 52 in second reactant compartment 50 and then through slit 23 in first layer 22 of outer containment envelope 20. If second reactant compartment 50 is disposed adjacent to slit 23 inside outer containment envelope 20, second reactant compartment 50 forms a barrier or dam that prevents reactants from escaping through slit 23. However, slit 23 nonetheless permits gasses to escape from inside outer containment envelope 20.

Figure 4A:
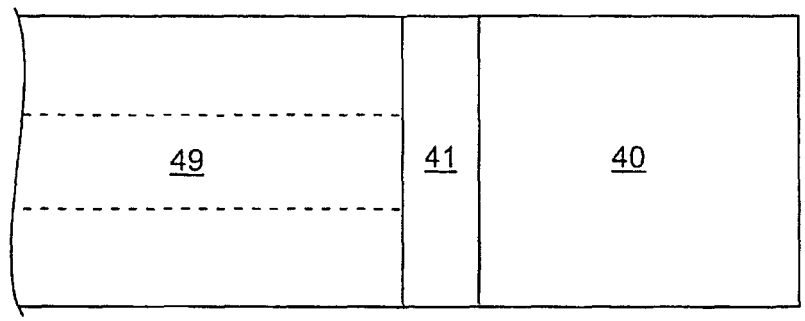
FIG. 4A is a top plan view of the sealed reactant compartment of the embodiment of FIG. 1.

To activate pouch 10, the user pulls on pull tab 30 which causes sealed reactant compartment 40 to shear open and empty its contents, in a process to be described in further detail below. To understand the pouch activation process, it is instructive to describe the construction of sealed reactant compartment 40 with reference to FIGS. 4A-4D. FIG. 4A shows a top view of sealed reactant compartment 40 with shearing material 49 connected thereto. Strips 46 and 48 are formed from shearing material 49 in a process described below. Sealed reactant compartment 40 and shearing material 49 (and thus, strips 46 and 48 as well) may all be integrally formed with one another, for example from a single sheet of polymeric film that is folded over upon itself and then sealed around its edges and at transverse seal 41. Shearing material 49 may comprise two layers of material corresponding to upper layer 42 and lower layer 44 of sealed reactant compartment 40. However, shearing material 49 may also each be formed of a single layer of material.

Figure 4B:
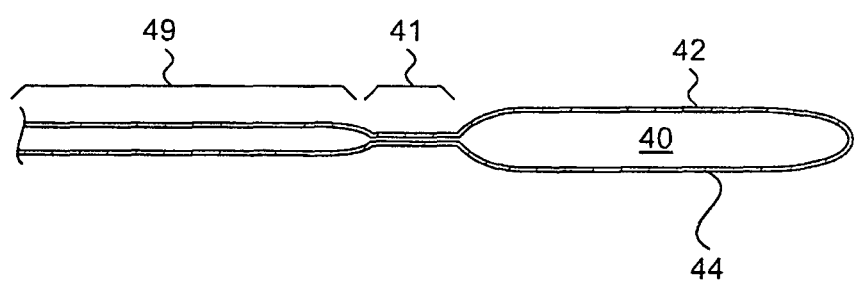
FIG. 4B is a cross-sectional view of the sealed reactant compartment of FIG. 4A.
Figure 4C:
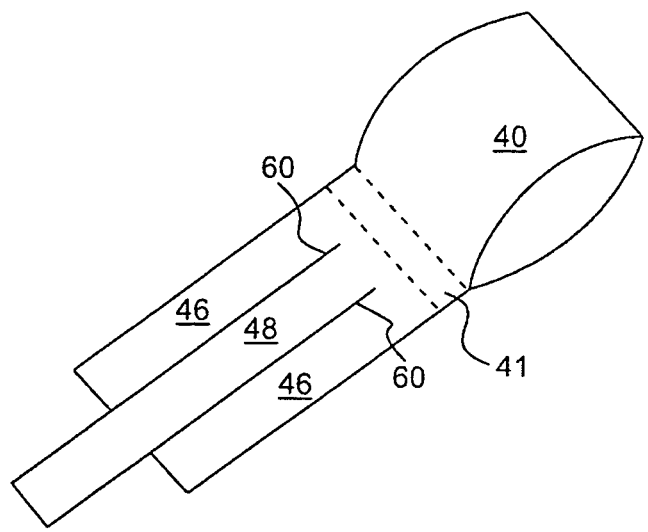
FIG. 4C is a perspective view of the sealed reactant compartment of FIG. 4A after three strips are formed.

The dashed lines in FIG. 4B represent pattern lines along shearing material 49. During manufacture of pouch 10, shearing material 49 is cut along the dashed pattern lines to form strips 46 and 48, as shown in FIG. 4C. Outer strips 46 are optionally trimmed in length relative to middle strip 48. Between outer strips 46 and middle strip 48 are shear lines 60. As used herein, the term "shear line" refers to a cut or tear in a material that will lengthen (i.e. propagate) in generally the same direction as the cut or tear when the material is subjected to shearing forces. Once a cut or tear in a material is established, very little shearing force is required to extend the shear line. As seen in FIG. 4C, sheer lines 60 terminate adjacent transverse seal 41. The region of seal 41 in the path of shear lines 60 is a predetermined failure region of sealed reactant compartment 40 because when a user applies shear force to the area (in a process described below) shear lines 60 will lengthen until they shear through transverse seal 41 thereby shearing open sealed reactant compartment 40.

Figure 4D:
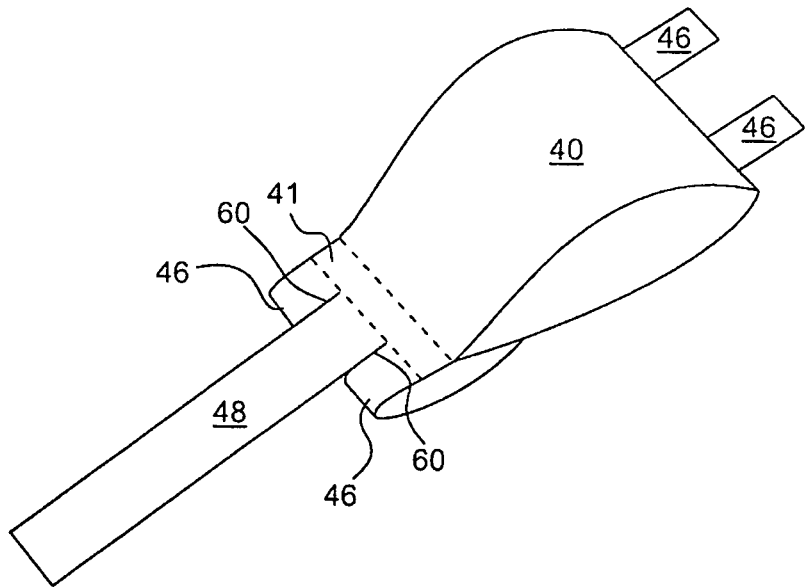
FIG. 4D is a perspective view of the sealed reactant compartment of FIG. 4C showing the two outer strips folded under the sealed reactant compartment.

As shown in FIG. 4D, once strips 46 and 48 are formed, outer strips 48 are folded under sealed reactant compartment 40, which is then installed into outer containment envelope 20 in this configuration. When sealed reactant compartment 40 is installed in outer containment envelope 20, the tips of outer strips 46 are anchored to outer containment envelope 20 so that outer strips 46 remain stationary relative to outer containment envelope 20. Thus, for the purposes of this discussion, outer strips 46 should viewed as immovable and fixed in place.

Figure 4E:
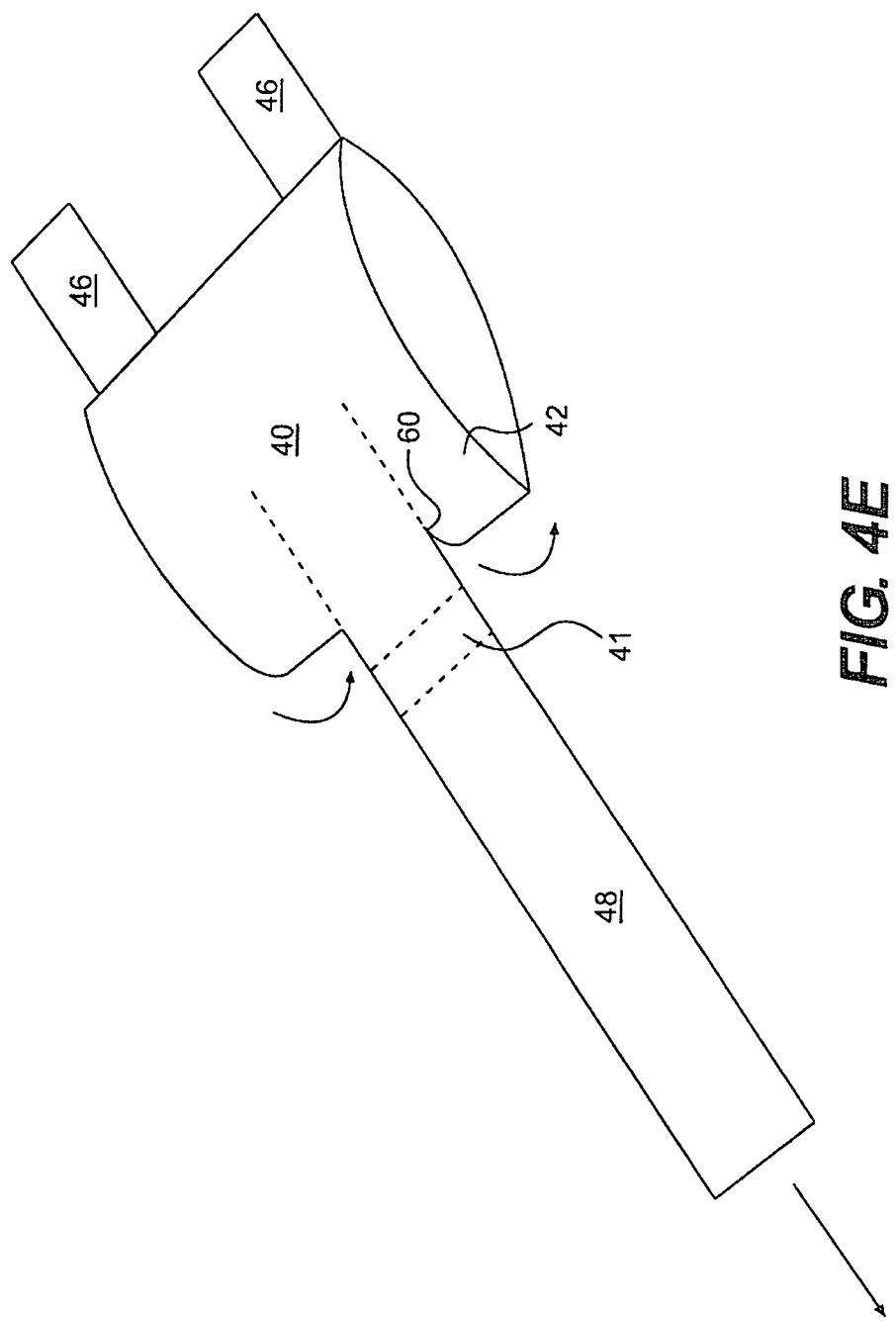
FIG. 4E is a perspective view of the sealed reactant compartment of FIG. 4C showing the sealed reactant compartment being shorn open by pulling on the middle shear strip.

The process of shearing open sealed reactant compartment 40 will now be described with reference to FIG. 4E. The user opens sealed reactant compartment 40 (i.e. the user activates pouch 10) by pulling on middle strip 48. Because outer strips 46 are anchored in place, the user's pulling force on middle strip 48 is converted into a shearing force along shear lines 60. The counterclockwise arrows in FIG. 4E indicate that as middle strip 48 moves to the left, upper layer 42 of sealed reactant compartment 40 in the region above outer strips 46 is caused to "roll over" and shear along shear lines 60. The dotted lines extending from shear lines 60 in FIG. 4E represent the path shear lines 60 will take if the user continues to pull on middle strip 48. Once shear lines 60 completely cross transverse seal 41 in the predetermined failure region, sealed reactant compartment 40 is violated and its contents are released.

Returning to FIG. 3, once the user pulls on pull tab 30 (which, as explained above, is attached to the tip of middle strip 48), sealed reactant compartment 40 will be shorn open and the reactant inside sealed reactant compartment 40 will be released into outer containment envelope 20 where it contacts a second reactant. If the second reactant is inside second reactant compartment 50, then second reactant compartment 50 is permeable to the reactant released from sealed reactant compartment 40. Any gases released by the chemical reaction of the first and second reactants may escape through slit 23 in outer containment envelope 20.

Figure 5A:
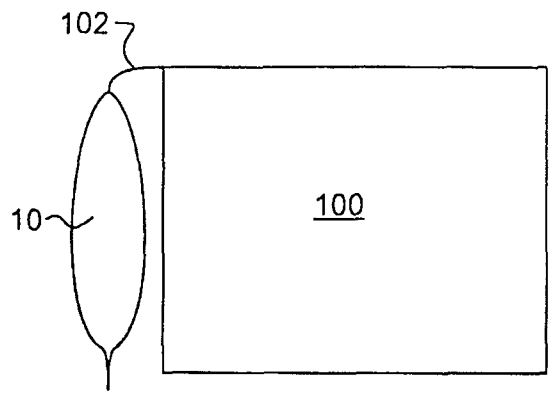
FIG. 5A is a side elevation view of the embodiment of FIG. 1 connected to an object by a hinge.
Figure 5B:
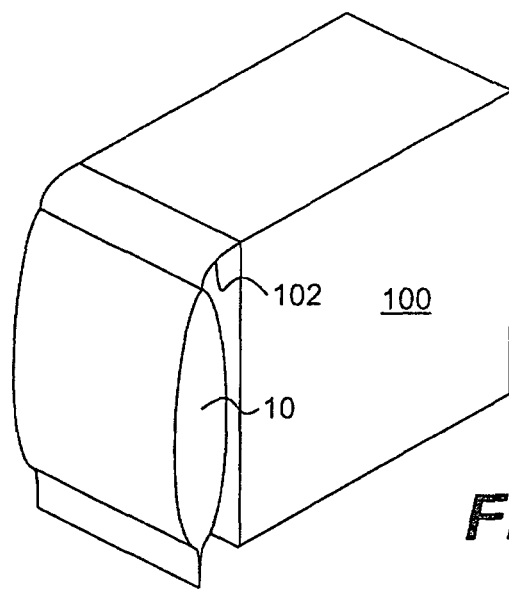
FIG. 5B is a perspective view of the embodiment of FIG. 5A.
Figure 5C:
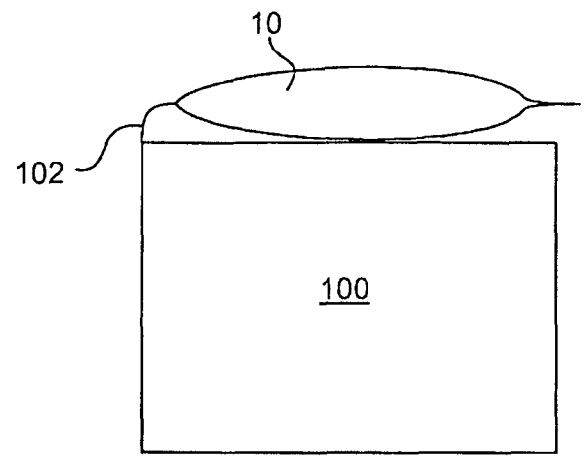
FIG. 5C is a side elevation view of the embodiment of FIG. 5A, showing the pouch hinged on top of the object.
Figure 5D:
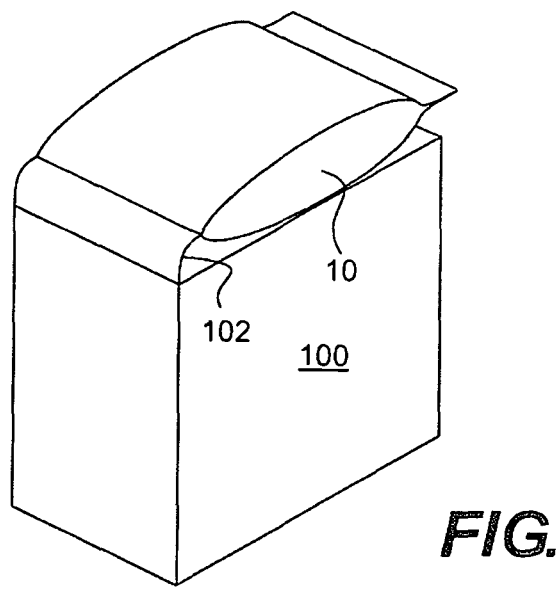
FIG. 5D is a perspective view of the embodiment of FIG. 5C.

One application of pouch 10 is to heat or cool objects by mounting pouch 10 on a surface of the object when pouch 10 contains exothermic or endothermic reactants. As shown in FIGS. 5A-D, pouch 10 is connected to object 100 by hinge 102. Hinge 102 may be a living hinge such as a sheet of plastic. When pouch 10 is activated it may be rotated about hinge 102 in order to rest on the top surface of object 100. Where object 100 is a container, any items inside object 100 (particularly items close to the top surface of object 100) will be heated or cooled by pouch 10. Although hinge 102 is shown in FIGS. 5C and 5D, the surface of pouch 10 contacting object 100 may comprise an adhesive so that pouch 10 may remain in contact with object 100 even if hinge 102 is not provided. It is to be understood that pouch 10 may be applied to any surface of object 100 by eliminating hinge 102 and adhering pouch 10 to the surface of object 100 desired to be heated. Pouch 10 may comprise a flat adhesive surface for application to object 100. Adhesives that may be used include thermal transfer silicone-based adhesives that help increase heat transfer between pouch 10 and object 100. Further, even if an adhesive is not used, other heat transfer compounds (including silicone-, non-silicone-, and metal-based compounds) may be used to increase heat transfer between pouch 10 and object 100.

Figure 6A:
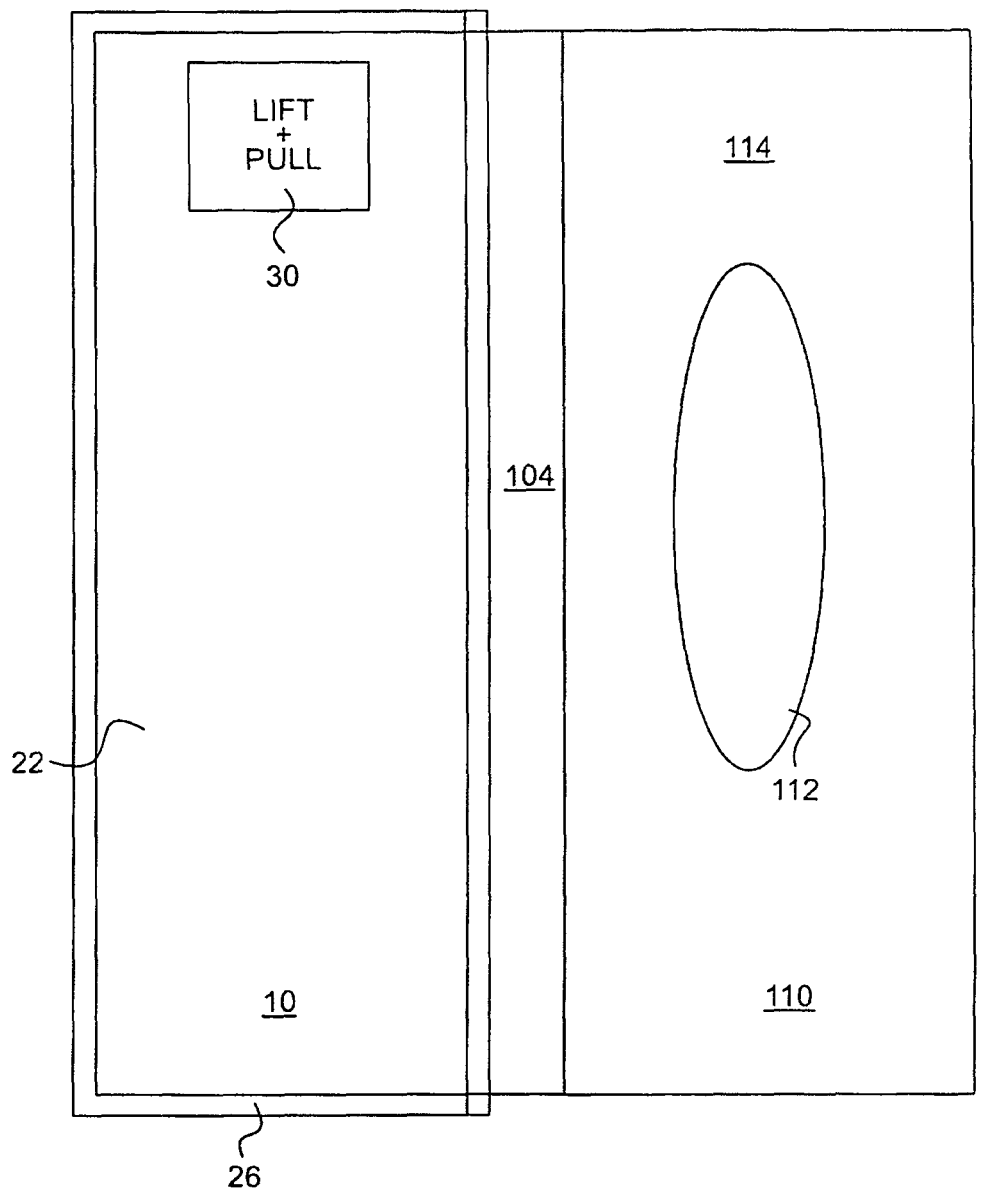
FIG. 6A is a top plan view of one embodiment of a self-heating wet wipe dispenser.

One type of object that pouch 10 may be applied to is a wet wipe (moistened towelette) dispenser. As shown in FIGS. 6A and 6B, pouch 10 is connected wet wipe dispenser 110 by living hinge 104. Pouch 10 can be rotated about living hinge 104 so that pouch 10 lies flat upon upper dispensing surface 114 of wet wipe dispenser 110, as shown in FIG. 6B. By placing pouch 10 on upper dispensing surface 114, wet wipes dispensed through aperture 112 of wet wipe dispenser 110 will be very warm (if pouch 10 contains exothermic reactants) almost immediately after application of pouch 10 to wet wipe dispenser 110. Alternatively, pouch 10 may be rotated under wet wipe dispenser 110 in order to heat the wet wipes from below.

Figure 7:
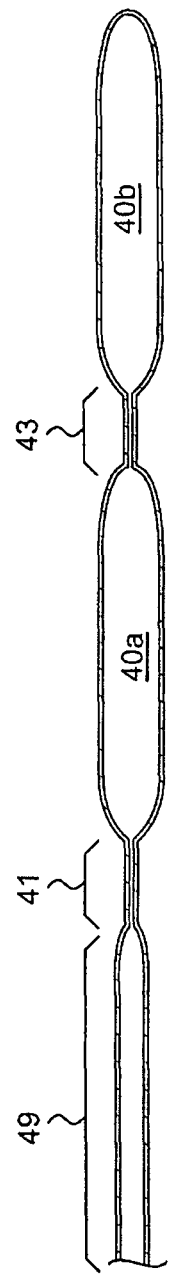
FIG. 7 is a cross-sectional view of a variation of the sealed reactant compartment of FIG. 4A.

Variations of a pouch for internal mixture of segregated reactants are of course contemplated. For example, sealed reactant compartment 40 may be converted into two sub-compartments 40a and 40b by placing second transverse seal 43 in the middle of sealed reactant compartment 40, as shown in FIG. 7. The same reactant, or two different reactants, may be contained in sub-compartments 40a and 40b. The contents of the two sub-compartments 40a and 40b are released into outer containment envelope 20 in the same way as previously described (i.e. by pulling on middle shear strip 48). The only difference is that here the user must take care to pull middle shear strip 48 far enough that shear lines 60 lengthen all the way across both transverse seal 41 and second transverse seal 43.

Another possible variation is to use fewer or greater than three strips to shear open sealed reactant compartment 40. For example, with reference to FIG. 4A, during construction of sealed reactant compartment 40, it is possible to only cut along one of the dashed pattern lines in shearing material 49 so that only two strips result. In that case one strip is folded under sealed reactant compartment 40 and anchored to the inside of outer containment envelope 20 (in the same way as described above with respect to outer strips 46). The other strip is the "pull strip" and extends out of slit 23 in outer containment envelope 20. When the user pulls on the strip, shearing will occur between the two strips until sealed reactant compartment 40 is shorn open. Similarly, more than three strips may also be used in other embodiments.

Persons of ordinary skill in the art are aware that countless other applications of pouch 10 are contemplated. For example, and without limitation, pouch 10 may include exothermic reactants and may be incorporated into self-heating paint cans in order to decrease paint viscosity in cold temperatures. Pouch 10 may simply be adhered to the bottom or walls of the paint can in order to transfer heat to the paint. Other self-heating objects such as self-heating medical devices and self-heating food and beverage containers may be produced in a similar manner.

The materials used to make pouch 10 are not critical and may include any suitable plastics, polymers, woven or non-woven fabrics, foils, or paper. Outer containment envelope 20 may be made from a liquid and gas impermeable material such as one or more sheets of plastic or foil. Outer containment envelope 20 may be made by folding a single sheet of material over upon itself and then bonding its edges together to form a sealed envelope, or by bonding two separate sheets together around their edges.

Sealed reactant compartment 40 may be made from any suitable material including an axially oriented polymeric film. Axially oriented films tear very easily in one direction and thus help shear lines 60 to propagate toward transverse seal 41 when the user pulls on middle strip 48. Axially oriented polymeric films may be made from polymers such as polypropylene, polystyrene and polyethylene, though this list is not exhaustive. Transverse seal 41 in sealed reactant compartment 40 may be made using any suitable technique including thermal or sonic welding or adhesives.

Second reactant compartment 50 is made from a material permeable to the reactant contained in sealed reactant compartment 40. For example, if sealed reactant compartment 40 contains a liquid such as salt water, second reactant compartment 50 may be made from nonwoven fibers or a mesh fabric. Other suitable materials for second reactant compartment 50 include substrates made from paper, cellulose and perforated plastics.

The reactants inside sealed reactant compartment 40 and second reactant compartment 50 may be reactants that undergo exothermic or endothermic chemical reactions when combined. However, the present embodiments are not limited by the types of reactants that may be used. The reactant in sealed reactant compartment 40 may be a liquid, solid (e.g. a powder) or gel, or any combination thereof. For example, and without limitation, the reactant may be fresh water, salt water, or a water-based gel created by adding absorbent particles to water (or gels created by any other method).

The disclosed embodiments of a pouch for internal mixture of segregated reactants have numerous advantages. Because transverse seal 41 of sealed reactant compartment 40 is broken by the user shearing rather than by crushing or twisting as is the case with a frangible seal, very little force is required to activate the pouch. Further, activation is very simple: the user simply pulls on a tab. There is no guesswork required of the user in terms of determining exactly where to apply force to the pouch in order to break the internal seals. Finally, because gasses are able to escape from outer containment envelope 20 through slit 23, a wide variety of reactants may be used as inflation and/or explosion of the pouch is not an issue.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A self-heating object, comprising a pouch and an object to be heated, wherein the pouch comprises:
    an outer containment envelope having a periphery, the outer containment envelope comprising a first layer bonded to a second layer around the periphery of the outer containment envelope, the first layer having a slit;
    a sealed reactant compartment disposed inside the outer containment envelope, the sealed reactant compartment containing a first reactant; and
    at least two strips connected to the sealed reactant compartment, the at least two strips comprising a shear strip separated from an outer strip by a shear line, the shear strip and the outer strip each having a tip, wherein the outer strip is folded under the sealed reactant compartment with its tip anchored to the outer containment envelope, and wherein the shear strip extends away from the sealed reactant compartment and through the slit in the first layer of the outer containment envelope so that the tip of the shear strip is disposed outside the outer containment envelope;
    wherein pulling on the tip of the shear strip causes the shear line to lengthen until the sealed reactant compartment is shorn open and releases the first reactant into the outer containment envelope; and
    a second reactant compartment disposed inside the outer containment envelope adjacent the first sealed reactant compartment and containing a second reactant, the second reactant compartment further comprising: a permeable membrane, and
    a slit passing completely through the second reactant compartment;
    wherein the shear strip passes through the slit in the second reactant compartment.

2. A self-heating object, comprising a pouch and an object to be heated, wherein the pouch comprises:
    an outer containment envelope having a periphery, the outer containment envelope comprising a first layer bonded to a second layer around the periphery of the outer containment envelope, the first layer having a slit;

a sealed reactant compartment disposed inside the outer containment envelope, the sealed reactant compartment containing a first reactant; and at least three strips connected to the sealed reactant compartment, the at least three strips comprising a middle shear strip separated from two outer strips by two shear lines, the middle shear strip and the two outer strips each having a tip, wherein the two outer strips are folded under the sealed reactant compartment with their tips anchored to the outer containment envelope, and wherein the middle shear strip extends away from the sealed reactant compartment and through the slit in the first layer of the outer containment envelope so that the tip of the middle shear strip is disposed outside the outer containment envelope; wherein pulling on the tip of the middle shear strip causes the two shear lines to lengthen until the sealed reactant compartment is shorn open and releases the first reactant into the outer containment envelope;

a second reactant compartment disposed inside the outer containment envelope adjacent the sealed reactant compartment and containing a second reactant, the second reactant compartment further comprising: a permeable membrane, and a slit passing completely through the second reactant compartment; wherein the middle shear strip passes through the slit in the second reactant compartment, wherein the pouch is connected to, or adhered to, the object to be heated.

3. The self-heating object of claim 2, wherein the first reactant is a liquid that is released onto the permeable membrane of the second reactant compartment when the middle shear strip is pulled, thereby mixing the first reactant with the second reactant.

4. The self-heating object of claim 3, wherein mixing the first reactant with the second reactant creates an exothermic reaction and the pouch emits heat.

5. The self-heating object of claim 4, wherein the pouch comprises a substantially flat adhesive surface, wherein the substantially flat adhesive surface of the pouch is adhered to the object to be heated.

6. The self-heating object of claim 5, wherein the pouch is adhered to the object to be heated with a thermal transfer silicone-based adhesive.

7. The self-heating object of claim 3, wherein mixing the first reactant with the second reactant creates an endothermic reaction and the pouch absorbs heat.

8. The self-heating object of claim 2, wherein the object to be heated is a wet wipe dispenser having a substantially flat dispensing surface with a dispensing aperture through which wet wipes are dispensed, and wherein the pouch is hinged to the wet wipe dispenser to permit the pouch to lie flat on the dispensing surface and to rotate off the dispensing surface to uncover the dispensing aperture.

9. A self-heating object, comprising a pouch and an object to be heated, wherein the pouch comprises:
an outer containment envelope having a periphery, the outer containment envelope comprising a first layer bonded to a second layer around the periphery of the outer containment envelope, the first layer having a slit;
a sealed reactant compartment disposed inside the outer containment envelope, the sealed reactant compartment containing a first reactant; and
at least three strips connected to the sealed reactant compartment, the at least three strips comprising a middle shear strip separated from two outer strips by two shear lines, the middle shear strip and the two outer strips each having a tip, wherein the two outer strips are folded under the sealed reactant compartment with their tips anchored to the outer containment envelope, and wherein the middle shear strip extends away from the sealed reactant compartment and through the slit in the first layer of the outer containment envelope so that the tip of the middle shear strip is disposed outside the outer containment envelope;

wherein pulling on the tip of the middle shear strip causes the two shear lines to lengthen until the sealed reactant compartment is shorn open and releases the first reactant into the outer containment envelope; and a second reactant compartment disposed inside the outer containment envelope adjacent the sealed reactant compartment and containing a second reactant, the second reactant compartment further comprising: a permeable membrane wherein the second reactant compartment forms a barrier that prevents the first reactant from escaping through the slit in the outer containment envelope after the tip of the middle shear strip is pulled.

10. A self-heating object, comprising a pouch and an object to be heated, wherein the pouch comprises:
an outer containment envelope having a periphery, the outer containment envelope comprising a first layer bonded to a second layer around the periphery of the outer containment envelope, the first layer having a slit;
a sealed reactant compartment disposed inside the outer containment envelope, the sealed reactant compartment containing a first reactant; and
at least three strips connected to the sealed reactant compartment, the at least three strips comprising a middle shear strip separated from two outer strips by two shear lines, the middle shear strip and the two outer strips each having a tip, wherein the two outer strips are folded under the sealed reactant compartment with their tips fixedly anchored to the outer containment envelope, wherein the middle shear strip is sealed between the two outer strips and extends away from the sealed reactant compartment and through the slit in the first layer of the outer containment envelope so that the tip of the middle shear strip is disposed outside the outer containment envelope;

wherein pulling on the tip of the middle shear strip causes the two shear lines to lengthen until the sealed reactant compartment is shorn open and releases the first reactant into the outer containment envelope but the tips of the outer strips remain fixed in place; and wherein the pouch is hinged or adhered to the object to be heated, wherein the middle shear strip further comprises an adhesive tab attached to the tip of the middle shear strip and adhered to an outer surface of the first layer of the outer containment envelope and around the slit in the first layer of the outer containment envelope to hermetically seal the slit in the first layer of the outer containment envelope.

11. A self-heating object, comprising a pouch and an object to be heated, wherein the pouch comprises:
an outer containment envelope having a periphery, the outer containment envelope comprising a first layer bonded to a second layer around the periphery of the outer containment envelope, the first layer having a slit;
a sealed reactant compartment disposed inside the outer containment envelope, the sealed reactant compartment containing a first reactant; and at least three strips connected to the sealed reactant compartment, the at least three strips comprising a middle shear strip separated from two outer strips by two shear lines, the middle shear strip and the two outer strips each having a tip, wherein the two outer strips are folded under the sealed reactant compartment with their tips fixedly anchored to the outer containment envelope, wherein the middle shear strip is sealed between the two outer strips and extends away from the sealed reactant compartment and through the slit in the first layer of the outer containment envelope so that the tip of the middle shear strip is disposed outside the outer containment envelope;

wherein pulling on the tip of the middle shear strip causes the two shear lines to lengthen until the sealed reactant compartment is shorn open and releases the first reactant into the outer containment envelope but the tips of the outer strips remain fixed in place, wherein the sealed reactant compartment comprises a first transverse seal that is broken by at least one of the at least two shear lines when the tip of the middle shear strip is pulled, and wherein the sealed reactant compartment further comprises first and second separate chambers separated by a second transverse seal that is broken by at least one of the at least two shear lines when the tip of the middle strip is pulled, the first chamber of the sealed reactant compartment containing the first reactant, the second chamber of the sealed reactant compartment containing a second reactant; and wherein the pouch is connected to, or adhered to, the object to be heated.

* * * * *